United States Patent
Buxade

Patent Number: 5,091,547
Date of Patent: Feb. 25, 1992

[54] PHENYLACETIC ACID DERIVATIVE AND PROCESS FOR MAKING SAME

[75] Inventor: Antonio Buxade, Barcelona, Spain

[73] Assignee: Laboratorias Vinas, S.A., Barcelona, Spain

[21] Appl. No.: 525,876

[22] Filed: May 17, 1990

[30] Foreign Application Priority Data

May 29, 1989 [ES] Spain ................................. 8901816

[51] Int. Cl.$^5$ ............................................. C07F 3/06
[52] U.S. Cl. ................................... 556/131; 556/122; 556/134; 514/925; 514/926
[58] Field of Search ............... 556/118, 121, 122, 130, 556/131, 132, 134; 514/925, 926, 927, 492, 494

[56] References Cited

U.S. PATENT DOCUMENTS

| Re. 32,909 | 4/1989 | Lionelle et al. | 514/494 X |
|---|---|---|---|
| 4,183,951 | 1/1980 | Lafon | 514/494 X |
| 4,342,767 | 8/1982 | Albers-Schonberg et al. | 556/131 X |
| 4,503,072 | 3/1985 | Hoffman et al. | 556/134 X |
| 4,695,587 | 9/1987 | Terahara et al. | 556/131 X |
| 4,701,448 | 10/1987 | Endo et al. | 514/494 X |
| 4,966,985 | 10/1990 | Hasegawa et al. | 556/134 X |
| 5,004,741 | 4/1991 | Evans et al. | 514/926 X |

FOREIGN PATENT DOCUMENTS 4885635 9/1980 Spain .

OTHER PUBLICATIONS 88500109.9, Solicitud de Patente Europea, Dr. Ing. M. Curell Sunol 11/14/88 Barcelona, Spain.

Primary Examiner—Arthur C. Prescott
Attorney, Agent, or Firm—Michael J. Striker

[57] ABSTRACT

A pharmaceutical phenylacetic acid derivative of the following formula (I):

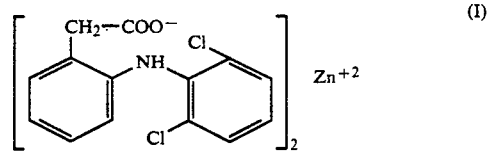

with the process of obtention which includes reacting 2-(2,6-dichloroaniline)-phenylacetic acid with zinc oxide, zinc hydroxides, zinc carbonates or zinc salts or reacting an ammonium salt, an alkali metal salt or an alkaline earth metal salt of 2-(2,6-dichloroaniline)-phenylacetic acid with a zinc salt, e.g. zinc chloride, in a nonpolar solvent. The compound of formula I is novel and has improved pharmaceutical properties in anti-inflammatory preparations.

2 Claims, No Drawings

PHENYLACETIC ACID DERIVATIVE AND PROCESS FOR MAKING SAME

BACKGROUND OF THE INVENTION

My invention relates to a procedure for preparation of a new phenylacetic acid derivative or, to be more specific, a zinc compound of 2-(2,6-dichloroaniline)-phenylacetic acid. This new compound is represented by the formula(I)

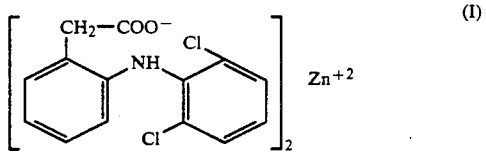

The compound, 2-(2,6-dichloroaniline phenylacetic acid, is known for its anti-inflammatory and antirheumatic properties and is generally administered in the form of its sodium salt, which enables it to be dissolved, since the acid as such is practically insoluble in water.

On the other hand zinc is known as a trace element which can be used both for the treatment of gastric and duodenal ulcers and for protection of the corresponding mucous membranes against aggressive agents and also in rheumatoid arthritis (European Patent No. 88500109.9 and Spanish Patent No. 488,563).

However, there have been no reports to date of derivative compounds which would permit the administration of both zinc and 2-(2,6-dichloroaniline)-phenylacetic acid in a single dose with beneficial results. This would, moreover, avoid the administration of other ions which are either unnecessary for reaching the required therapeutic activity or may have some other kind of undesired activity.

SUMMARY OF THE INVENTION

It is an object of my invention to provide a single derivative compound represented by the formula (I):

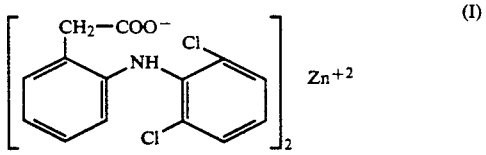

The new compound of formula (I) allows patients to be given both the aforementioned constituents, that is, 2-(2,6-dichloroaniline)-phenylacetic acid and zinc, together in a single dose without the other ions that would be present in a mixture of compounds containing each constituent.

Apart from this advantage in its administration, the new compound developed and described in this invention has been shown to have an anti-inflammatory, antirheumatic and protective action, which is another advantage over the acid itself and other cationic derivatives. This is particularly important if one considers that one of the most undesirable effects of the latter is precisely their gastric intolerance, which often means treatment has to be stopped, especially in chronic cases.

This new derivative is novel. Furthermore it can be used as an active constituent with therapeutic application not only in patients who cannot tolerate the aforesaid anti-inflammatory preparation and its other salts, but also in patients under regular treatment with them, thereby avoiding this type of side effect.

The process for making the new compound of the formula (I) according to my invention comprises the steps of reacting 2-(2,6-dichloroaniline)-phenylacetic acid of formula (II)

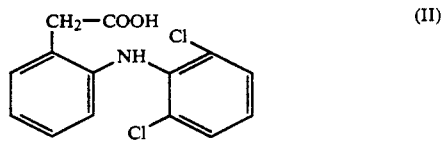

with zinc oxide, zinc hydroxides, zinc carbonates or zinc salts. Also according to the invention, the new compound of the formula (I) can be obtained by reacting a corresponding salt of the 2-(2.6-dichloroaniline) phenylacetic acid (as such as prepared in situ and unisolated) which may be an ammonium, alkaline or alkaliearth salt, with a zinc salt. The zinc salt may be a chloride, nitrate, sulphate, phosphate or the like. The reagent may be present in equimolar amounts and also in greater or lesser quantity in relation to the substrate.

Preferably, the process is based on an alkali metal or ammonium salt(as such or produced in situ) and equimolar amounts of zinc chloride or nitrate.

The reaction may be carried out in a solvent or mixture of polar solvents, preferably in water or in a mixture of water and low molecular weight alcohols.

The reaction temperature may be ambient temperature up to the reflux temperature of the solvent or solvents mixture. Nevertheless, the working temperature range is important, since depending on this parameter different crystalline forms can be obtained with different degrees of moisture. Thus, when the reaction is carried out between 60° C. and the solvent's reflux temperature, the zinc derivative obtained is the anhydrous salt, while the same reaction carried out at near-ambient temperatures (10°-25° C.) produces the derivative hydrated basically with 3 and ½ molecules of water.

The importance of controlling the reaction temperature lies in the fact that the anhydrous and hydrated forms possess certain different physical and chemical properties which can affect both the bioavailability and, for example, the wettability-solubility, and therefore give rise to some differences in their pharmacological activity, as well as affecting the facility of their industrial processing, which inevitably influences the cost of the end product.

The zinc reagent may be added as follows: as a solid, bit by bit; dissolved in the solvent whenever that reagent is soluble; and in the form of a paste or suspension in the solvent.

The compound may be crystallized or precipitated out. For reasons of purity crystallization is preferred. It is subsequently filtered and dried.

The zinc derivative of the 2-(2,6-dichloroaniline)-phenylacetic acid make according to this process is, both in its anhydrous form and its hydrated form, extremely water-insoluble, unlike the known sodium salt.

Three examples of the process of our invention for making the compound of formula (I) are set forth in the following.

EXAMPLES

Example 1

To a solution consisting of 4.0 g (12.6 mmol) of 2-(2,6-dichloroaniline) sodium phenylacetate in 300 ml of water at 60° C., is added another solution of 0.86 g (6.3 mmol) of zinc chloride in water. After addition the reaction is maintained for one hour at 60° C., following which it is filtered and the solid washed and then dried at 50° C. This process yields a white or ivory-colored crystalline solid with the following characteristics:

Water solubility: 1–5/10,000 (units of weight)
Alcohol solubility: 10–50/10,000 (units of weight)
Melting point: 252°–256° C.
IR(KBr): 3324, 1626, 1579, 1542, 1453, 1394, 1294 and 742 cm$^{-1}$.
Elemental analysis for $C_{28}H_{20}Cl_4N_2O_4Zn$:

|  | C | H | Cl | N | Zn |
|---|---|---|---|---|---|
| Calculated (%) | 51.29 | 3.07 | 21.63 | 4.27 | 9.97 |
| Found (%) | 51.43 | 3.21 | 21.48 | 4.25 | 10.05 |

Example 2

To a solution consisting of 1.5 g (5.0 mmol) of 2-(2,6-dichloroaniline)-phenylacetic acid in 200 ml of ethanol at 96.5° C. is added 0.50 g( 5.0 mmol) of zinc hydroxide and the mixture is kept at reflux for one hour. It is then filtered and the filtrate allowed to cool and crystallize. The solid is filtered, washed and allowed to dry at 40° C.

This process gives a white, crystalline solid with the same characteristics as that of the previous example.

Example 3

To a solution of 4.0 g (12.6 mmol) of 2-(2,6-dichloroaniline) sodium phenylacetate in 120 ml of a 70/50 water/methanol mixture at ambient temperature(15° to 20° C.) is added another another solution of 0.86 anhydrous zinc chloride in 50 ml of water. Following addition the reaction mixture is agitated or stirred and at the aforementioned temperature for one hour, after which it is filtered, the solid washed and then dried at ambient temperature for 24 hours. This process gives a white or ivory-colored crystalline solid with the following characteristics:

Water solubility: 1–5/10,000 (units of weight)
Alcohol solubility: 10–15/100 (units of weight)
Melting point: 250°–254° C.
IR(KBr): 3700–2800, 3281, 1578, 1561, 1510, 1453, 1453, 1403, 1304, 1201, 840, 770 and 750 cm$^{-1}$.
Water(K-F): 8.9–9.2%
Loss of volatiles($P_2O_5$, 60° C., vacuum): 8.9–9.1%
Elemental analysis for $C_{28}H_{20}Cl_4N_2O_4Zn$:

|  | C | H | Cl | N | Zn |
|---|---|---|---|---|---|
| Calculated (%) | 51.29 | 3.07 | 21.63 | 4.27 | 9.97 |
| Found (%) | 51.17 | 2.90 | 21.85 | 4.12 | 9.83 |

PHARMACOLOGICAL ACTIVITY

As explained previously, the compound of formula (I), which shall henceforth be referred to herein as LV-216, combines the advantage of anti-inflammatory and protective action. It is worth noting that in rats with ulcers induced by ethanol, at doses of between 5 and 15 mg/kg of the new compound the protective action attained inhibition of as much as 80%.

Likewise, the compared anti-inflammatory and ulcerogenic activities of LV-216, sodium salt of 2-(2,6-dichloroaniline)-phenylacetic acid (hereinafter "sodium salt" and sodium salt + zinc have been studied, showing surprising results and an unexpectedly superior protective effect concerning the ulcerogenic action.

The pharmacological test results for the product LV-216 are set out below.

A) Anti-inflammatory Action

The anti-inflammatory action of LV-216 has been studied in the carragheenin oedema described by Winter, et al. (Proc. Soc. Exp. Biol. Med. 111: 544, 1962), using Wistar rats weighing 170±20 g. The inflammation was induced by intradermal injection of a suspension of carragheenin into the plantar pad and the volume of the paw was measured by plethysmography. The anti-inflammatory effect was assessed by calculating the percentage of inhibition of the inflammation in the groups treated, compared to the control group.

The results obtained with the LV-216 show a 55% inhibition of inflammation at a dose of 11 mg/kg, for the anhydrous LV-216 and 66% for the hydrated LV-216.

B) Protective Activity

Using the experimental model of ulcers induced by absolute ethanol described by Rober et al (Gastroenterology, 77: 433, 1979) the cytoprotective activity of LV-216 was compared with that of 2-(2,6-dichloroaniline)-phenylacetic acid at equimolecular doses and with a control group that was given only excipient.

The enclosed protective activity table shows the lesion indices(in ulcerated mm) for the groups studied, as well as the percentages of ulcer inhibition in the groups treated compared with the control group(average values subject to mean error).

TABLE I

| PROTECTIVE ACTIVITY | | |
|---|---|---|
|  | mm lesion | % inhibition |
| Control | 86.3 ± 9.4 | — |
| 2-(2,6-dichloroaniline)-phenylacetic acid (sodium salt) | 70.8 ± 8.2 | 17.9 |
| LV-216 (11 mg/kg) | 36.1 ± 8.9 a, b | 58.2 | t test
a = $p < 0.01$ versus control
b = $p < 0.05$ versus 2-(2,6-dichloroaniline)-phenylacetic acid (sodium salt).

As can be seen, the starting acid does not inhibit the ulcers induced by absolute ethanol, while the LV-216 produces over 50% inhibition, which is statistically significant with regard to the control group and to t he group treated with the acid.

C. Comparative Ulcerogenic Action of LV-216

A comparative study of the ulcerogenic action of LV-216, sodium salt and sodium salt + zinc was performed. The group of animals treated with sodium salt + zinc, both constituents separately, was introduced to compare it with the group treated with LV-216 alone, a derivative compound in which both therapeutic constituents are present in one and the same molecule.

Female Wistar rats of 195±15 g body weight were used for the experiment and were distributed in accordance with the following method:

Group I: control (excipient) (n=8)
Group II: sodium salt 10 mg/kg (n=8)
Group III: LV-216 11 mg/kg (n=8)
Group IV: sodium salt 10 mg/kg+zinc sulphate 2.5 mg/kg (n=8) (equivalent doses).

The products were administered orally every day for four consecutive days. The animals were given no food during the 24 hours prior to the last dose. Three hours after this last dose the rats were examined and the ulcerous lesions that had appeared in the stomach and intestine (duodenum, jejunum and proximal section of the ileum) were submitted to examination as per Adami's criterion(Arch. Int. Pharmacodyn.; 147, 113-145, 1964).

The following table II shows the macroscopic lesion indices corresponding to the different groups of animals studied.

TABLE II

Compared Ulcerogenic Action of LV-216, /* and /* + zinc. Macroscopic Lesion Indices.

|  | Control | SS | LV-216 | SS + Zn |
|---|---|---|---|---|
| x ± e | 0.4 ± 0.2 | 4.0 ± 0.4 | 1.1 ± 0.3 | 2.2 ± 0.6 |
| t vs CONTROL |  | *** | NS |  |
| t vs SS |  |  | *** | * |

SS = sodium salt
* $p < 0.05$;
*** $p < 0.001$

The results set out in Table II show substantial differences in ulcerous indices among the groups studied. The rats treated with sodium salt present ulcerous lesions in the stomach and intestine, the differences being statistically significant versus the control groups. Significant differences versus the control were also observed in the animals that were given sodium salt+zinc, although the ulcerous index is lower than that of the sodium salt. On the other hand, treatment with LV-216 gave an average ulcerous index of 1.1, far below those obtained in the other groups treated and not significant versus the control.

These results indicate that the LV-216 possesses a surprisingly high degree of gastric tolerance, greater than that shown by the sodium salt administered alone or in combination with Zinc. We can therefore observe a synergistic effect of the LV-216 in comparison with sodium salt and zinc, which was unpredictable, as the tolerance increases when this new zinc derivative is administered.

This synergistic effect regarding the gastric tolerance in the ulcerogenic action is all the more surprising considering both the insolubility (lower bioavailability) of the new zinc derivative (LV-216) and the amount of zinc (1.1 mg/kg) corresponding to the dose of LV-216 administered compared to the usual pharmacological doses of other zinc derivatives (15 to 40 mg/kg).

These results therefore show that the compound of formula I is a new different compound having better pharmacological properties than compounds containing its constituents.

Pharmaceutically Acceptable Forms

For therapeutic purposes the new zinc compound derived from 2-(2,6-dichloroaniline) phenylacetic acid as per formula (I), according to my invention, will normally be administered in pharmaceutical forms that include as the essential active ingredient at least the aforesaid compound, either on its own or in associated with a pharmaceutical vehicle.

The pharmaceutical vehicle may be a solid, a liquid or a mixed vehicle. For example, solid vehicles may be lactose, terra alba, saccharose, talc, gelatine, agar-agar, pectin, acacia, magnesium stearate, stearic acid and the like. Examples of liquid vehicles are: syrup, peanut oil, olive oil, water and the like.

Evidently a wide variety of pharmaceutical forms are possible. So, if a solid vehicle is used, the formula I compound can be made up in tablets, encapsulated in hard gelatine, or prepared as powder, granules, pills, etc.

If a liquid vehicle is used, the preparation containing the active constituent of formula (I) can be made up in the form of a syrup, emulsion, soft gelatin capsule, injectable sterile liquid solution in ampules or an aqueous or nonaqueous liquid suspension, and the like.

When mixed vehicles are used the formula I compound can be presented in the form of creams, ointments, suppositories and the like.

Using any of the pharmaceutical vehicles mentioned above—solid, liquid or mixed—the active compound referred to in this invention can also be formulated for delayed action by oral administration or topical application.

The pharmaceutical forms are prepared according to conventional galenic techniques involving procedures such as mixing, granulation and pressing, dispersion or dissolving of the ingredients depending on the type of preparation required.

The effective amount of active ingredient present in the pharmaceutical form will vary between 50 and 500 mg depending on the patient's condition and on the doctor's judgement. The means of administration is not restricted and may be, among others, oral, parenteral, rectal, topical and the like.

Other pharmacologically-active compounds may be included in one and the same pharmaceutical form.

While the invention has been illustrated and described as embodied in a new phenylacetic acid derivative and process for making same, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims.

I claim:

1. A zinc derivative of 2-(2,6-dichloroaniline)-phenylacetic acid having the following formula (I):

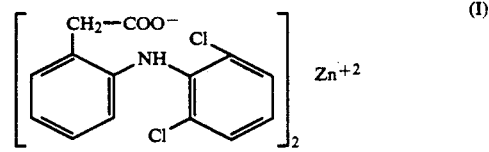

2. A pharmaceutical composition with anti-inflammatory and protector gastric properties, comprising an effective amount of the zinc derivative as defined in claim 1 and a pharmaceutically acceptable carrier.

* * * * *